US00PP18445P2

(12) United States Plant Patent
Jepsen

(10) Patent No.: US PP18,445 P2
(45) Date of Patent: Jan. 22, 2008

(54) *KALANCHOE* PLANT NAMED 'ARINA'

(50) Latin Name: *Kalanchoe blossfeldiana*
Varietal Denomination: Arina

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 73 days.

(21) Appl. No.: 11/259,311

(22) Filed: Oct. 26, 2005

(51) Int. Cl.
*A01H 5/00* (2006.01)

(52) U.S. Cl. ..... Plt./335
(58) Field of Classification Search ..... Plt./335, Plt./340
See application file for complete search history.

(56) References Cited

PUBLICATIONS

UPOVROM Plant Variety database search 2006/04 search for 'Pachafvel'.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of *Kalanchoe* plant named 'Arina', characterized by its compact, upright and freely branching plant habit; relatively small dark green-colored leaves; dark orange-colored single flowers; and excellent postproduction longevity.

1 Drawing Sheet

Botanical designation: *Kalanchoe blossfeldiana.*
Cultivar denomination: 'Arina'.

BACKGROUND OF THE INVENTION

The present invention relates to a new and distinct cultivar of *Kalanchoe* plant, botanically known as *Kalanchoe blossfeldiana,* and hereinafter referred to by the name 'Arina'.

The new *Kalanchoe* is a product of a planned breeding program conducted by the Inventor in Hinnerup, Denmark. The objective of the breeding program was to create new freely-flowering *Kalanchoe* cultivars with attractive flower coloration and excellent postproduction longevity.

The new *Kalanchoe* originated from a cross-pollination made in Hinnerup, Denmark in February, 2000, of the *Kalanchoe blossfeldiana* cultivar Pico, not patented, as the female, or seed, parent with the *Kalanchoe blossfeldiana* cultivar Fame, disclosed in U.S. Plant Pat. No. 9,429, as the male, or pollen, parent. The new *Kalanchoe* was discovered and selected by the Inventor as a single flowering plant within the progeny of the stated cross-pollination grown in a controlled environment in Hinnerup, Denmark in April, 2001.

Asexual reproduction of the new *Kalanchoe* by terminal cuttings at Hinnerup, Denmark since July, 2001, has shown that the unique features of this new *Kalanchoe* are stable and reproduced true to type in successive generations.

BRIEF SUMMARY OF THE INVENTION

The cultivar Arina has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Arina'. These characteristics in combination distinguish 'Arina' as a new and distinct cultivar:

1. Compact, upright and freely branching plant habit.
2. Relatively small dark green-colored leaves.
3. Dark orange-colored single flowers.
4. Excellent postproduction longevity.

Plants of the new *Kalanchoe* differ primarily from plants of the female parent, the cultivar Pico, in the following characteristics:

1. Plants of the new *Kalanchoe* are stronger than plants of the cultivar Pico.
2. Plants of the new *Kalanchoe* have darker green-colored leaves than plants of the cultivar Pico.
3. Plants of the new *Kalanchoe* have darker orange-colored flowers than plants of the cultivar Pico.

Plants of the new *Kalanchoe* differ primarily from plants of the male parent, the cultivar Fame, in the following characteristics:

1. Plants of the new *Kalanchoe* have smaller flowers than plants of the cultivar Fame.
2. Plants of the new *Kalanchoe* have darker orange-colored flowers than plants of the cultivar Fame.

Plants of the new *Kalanchoe* can be compared to plants of the *Kalanchoe* cultivar Carmen, disclosed in U.S. Plant Pat. No. 15,838. In side-by-side comparisons conducted in Hinnerup, Denmark, plants of the new *Kalanchoe* differed from plants of the cultivar Carmen in the following characteristics:

1. Plants of the new *Kalanchoe* were more compact and had shorter internodes than plants of the cultivar Carmen.
2. Plants of the new *Kalanchoe* had smaller leaves than plants of the cultivar Carmen.

3. Plants of the new *Kalanchoe* had smaller and fewer flowers than plants of the cultivar Carmen.
4. Plants of the new *Kalanchoe* flowered about four days later than plants of the cultivar Carmen.
5. Plants of the new *Kalanchoe* had darker orange-colored flowers than plants of the cultivar Carmen.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe.* The photographs were taken under diffuse natural light conditions on a sunny day at approximately noon in Hinnerup, Denmark.

The photograph at the top of the sheet comprises a side perspective view of a typical flowering potted plant of 'Arina'.

The photograph at the bottom of the sheet comprises a top perspective view of a typical flowering plant of 'Arina'.

DETAILED BOTANICAL DESCRIPTION

In the following description, color references are made to The Royal Horticultural Society Colour Chart, 2001 Edition, except where general terms of ordinary dictionary significance are used. Plants used in the photographs and for the following observations and measurements were grown in Hinnerup, Denmark, under commercial practice in a glass-covered greenhouse for about 14 weeks after planting with average day temperatures of 19° C., average night temperatures of 21° C. and light levels ranging from 10 to 50 kilolux. Plants used for the description and photographs were not pinched. Unless otherwise specified, the leaf description represents leaves from a vegetative plant.

Botanical classification: *Kalanchoe blossfeldiana* cultivar Arina.

Parentage:

*Female, or seed, parent.*—*Kalanchoe blossfeldiana* cultivar Pico, not patented.

*Male, or pollen, parent.*—*Kalanchoe blossfeldiana* cultivar Fame, disclosed in U.S. Plant Pat. No. 9,429.

Propagation:

*Type cutting.*—Terminal cuttings.

*Time to initiate roots, summer.*—About two weeks at 19° C. to 21° C.

*Time to initiate roots, winter.*—About three weeks at 19° C. to 21° C.

*Time to produce a rooted young plant, summer.*—About three weeks at 19° C. to 21° C.

*Time to produce a rooted young plant, winter.*—About four weeks at 19° C. to 21° C.

*Root description.*—Fine, fibrous; white, close to 155D, in color.

*Rooting habit.*—Freely branching; dense.

Plant description:

*Form/growth habit.*—Compact and upright plant habit; short internodes; freely flowering habit with numerous compound cymes. Actual plant shape will depend on whether or not plants are pinched (terminal apices removed). Moderately vigorous.

*Branching habit.*—About six lateral branches per plant. Pinching is not required but will enhance lateral branch development.

*Plant height at flowering.*—About 9 cm.

*Plant diameter at flowering.*—About 12 cm.

*Lateral branch description.*—Length: About 1.5 cm to 2.5 cm. Diameter: About 2 mm. Internode length: About 1 cm. Strength: Strong. Texture: Smooth, glabrous. Color: 146B.

*Foliage description.*—Arrangement: Opposite, simple. Size: Leaf size is reduced at floral induction. Vegetative plants: Length: About 7 cm to 10 cm. Width: About 5 cm to 6 cm. Reproductive plants: Length: about 6 cm to 8 cm. Width: About 5 cm. Shape: Ovate. Apex: Rounded. Base: Rounded. Margin: Crenate. Aspect: Concave. Texture, upper and lower surfaces: Smooth, glabrous; leathery; succulent. Color: Developing and fully expanded foliage, upper surface: 147A; shiny. Developing and fully expanded foliage, lower surface: 147C. Petiole length: About 5 cm to 6 cm. Petiole diameter: About 5 mm to 7 mm. Petiole texture, upper and lower surfaces: Smooth, glabrous. Petiole color, upper surface: 144A. Petiole color, lower surface: 147B.

Flower description:

*Flower type and habit.*—Small single flowers arranged in compound dichasial cymes that arise from leaf axils. Freely flowering habit. Flowers not persistent.

*Natural flowering season.*—Flowering year-round when flower initiation and development is induced under short day/long night conditions. In the garden, plants flower from April to October in Denmark.

*Time to flower.*—About 72 days with short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About 1.5 weeks after the first flower has opened, about 50% of the flowers are open.

*Post-production longevity.*—Plants of the new *Kalanchoe* maintain good leaf and flower substance for about six weeks under interior environmental conditions.

*Cyme height.*—About 4 cm to 5 cm.

*Cyme diameter.*—About 6 cm.

*Flowering habit.*—Freely flowering, potentially about 150 to 200 flowers per plant.

*Flower buds.*—Shape: Narrowly ellipsoidal. Length: About 1.7 cm. Width: About 3 mm. Color: 29D; towards the apex, 31B.

*Flower diameter.*—About 1.5 cm.

*Flower depth (height).*—About 1 cm.

*Petals.*—Quantity: About four per flower. Length: About 6 mm. Width: About 5 mm. Shape: Round ovate. Apex: Mucronate. Base: Fused. Margin: Entire. Texture, upper and lower surfaces: Glabrous, smooth. Color: When opening, upper surface: Towards the apex, 33A; towards the base, 28A. When opening, lower surface: 32A. Fully opened, upper surface: 33A; color becoming closer to 27A towards the base with development. Fully opened, lower surface: 29D overlain with 34A; color becoming closer to 27A blushed with 33C with development.

*Sepals.*—Quantity: About four per flower. Length: About 6 mm. Width: About 3 mm. Shape: Linear to lanceolate. Apex: Acute. Base: Truncate. Margin: Entire. Texture, upper and lower surfaces: Glabrous, smooth. Color: When opening and fully opened, upper surface: 143C. When opening and fully opened, lower surface: 143C.

*Peduncles.*—Length: About 2 cm. Diameter: About 3 mm. Angle: Erect to about 60° from vertical. Strength: Strong. Texture: Smooth, glabrous. Color: 137B.

*Pedicels.*—Length: About 3 mm. Diameter: About 1 mm. Angle: Erect to about 90° from vertical. Strength: Strong. Texture: Smooth, glabrous. Color: 137B.

*Reproductive organs.*—Stamens: Stamen number: About five to ten per flower. Anther length: About 1 mm. Anther shape: Elliptic. Anther color: 14B. Pollen amount: Moderate. Pollen color: 17C. Pistils: Pistil number: About four per flower. Pistil length: About 5 mm. Style length: About 2 mm. Style color: 145A. Stigma shape: Round. Stigma color: 145A. Ovaries: Superior and four-celled. Ovary color: Between 147A and 147B.

*Seeds.*—Quantity: About 50 to 60 seeds per ovary. Length: Less than 1 mm. Diameter: Less than 1 mm. Color, immature: 145C. Color, mature: 177A.

Disease/pest resistance: Resistance to known pathogens and pests common to *Kalanchoe* has not been observed on plants of the new *Kalanchoe* grown under commercial greenhouse conditions.

Temperature tolerance: Plants of the new *Kalanchoe* have been observed to tolerate temperatures from 5° C. to 30° C.

It is claimed:

1. A new and distinct cultivar of *Kalanchoe* plant named 'Arina', as illustrated and described.

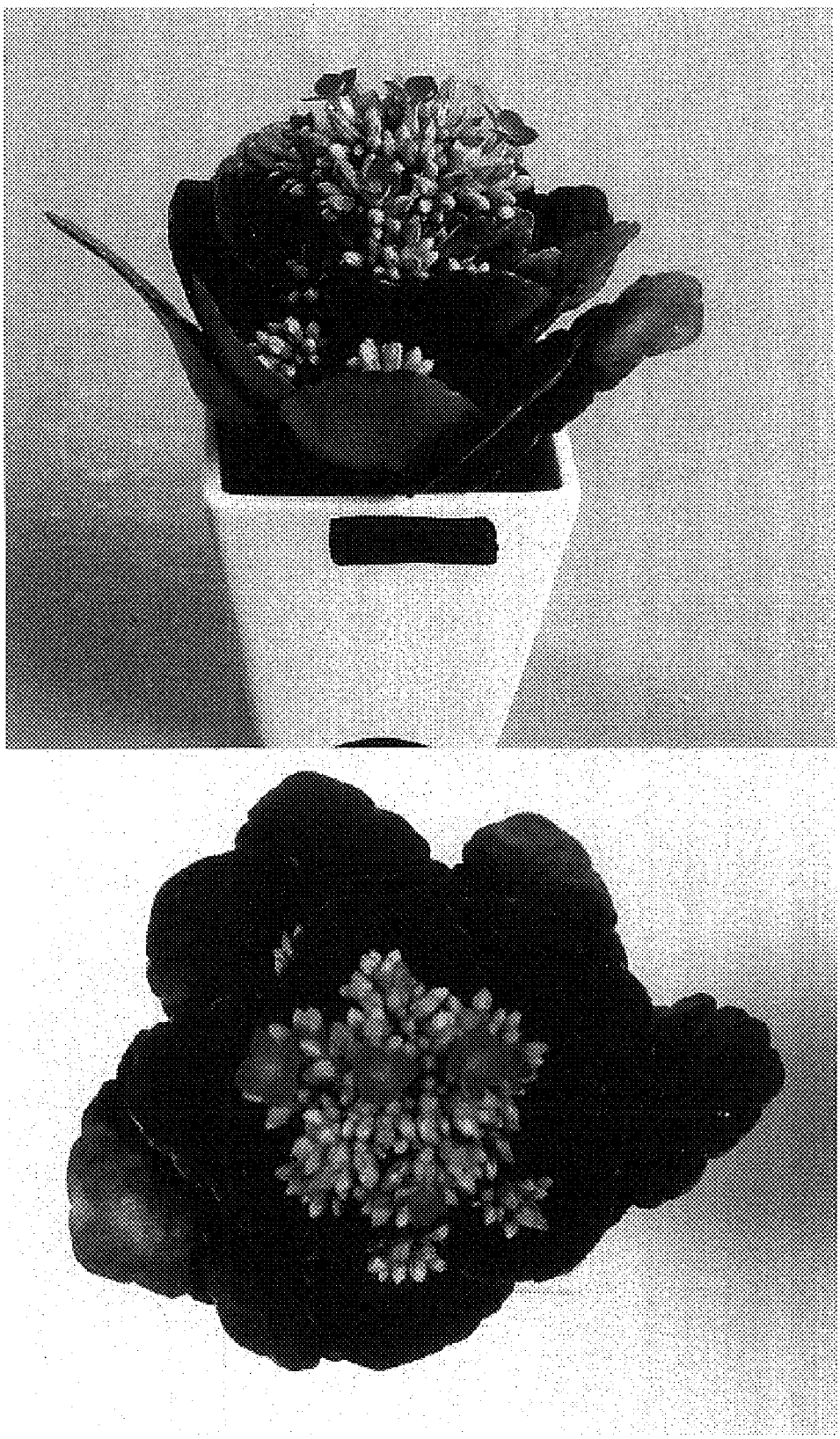

* * * * *